(12) United States Patent
McIntyre

(10) Patent No.: US 9,086,639 B2
(45) Date of Patent: Jul. 21, 2015

(54) FABRICATION OF ON-PRODUCT ABERRATION MONITORS WITH NANOMACHINING

(71) Applicant: International Business Machines Corporation, Armonk, NY (US)

(72) Inventor: Gregory R. McIntyre, Clifton Park, NY (US)

(73) Assignee: International Business Machines Corporation, Armonk, NY (US)

(*) Notice: Subject to any disclaimer, the term of this patent is extended or adjusted under 35 U.S.C. 154(b) by 28 days.

(21) Appl. No.: 14/024,659

(22) Filed: Sep. 12, 2013

(65) Prior Publication Data

US 2015/0070713 A1    Mar. 12, 2015

(51) Int. Cl.
*G01B 11/14* (2006.01)
*G03F 1/82* (2012.01)
*G01N 21/956* (2006.01)

(52) U.S. Cl.
CPC ............ *G03F 1/82* (2013.01); *G01N 21/956* (2013.01); *G01N 2021/95676* (2013.01)

(58) Field of Classification Search
CPC .............. G21G 5/00; G01B 5/28; G03F 1/00; G12B 21/08
USPC ................... 356/237.1–237.6, 625
See application file for complete search history.

(56) References Cited

U.S. PATENT DOCUMENTS

| | | | |
|---|---|---|---|
| 6,171,739 B1 | 1/2001 | Spence et al. | |
| 7,108,798 B2 * | 9/2006 | Ludwig et al. | 216/52 |
| 7,571,639 B2 | 8/2009 | Doi et al. | |
| 7,691,541 B2 | 4/2010 | Crocker et al. | |
| 2006/0147814 A1 * | 7/2006 | Liang | 430/5 |
| 2007/0166629 A1 * | 7/2007 | Kanamitsu | 430/5 |
| 2011/0027698 A1 * | 2/2011 | Park et al. | 430/5 |
| 2011/0165504 A1 * | 7/2011 | Ikuta | 430/5 |
| 2011/0303062 A1 | 12/2011 | Robinson | |

OTHER PUBLICATIONS

P. Dirksen et al., "Aerial image based lens metrology for wafer steppers," SPIE 31st International Symposium on Advanced Lithography, 2006, 61540X, 11 pages.

T. Brunner et al., "Quantitative stepper metrology using the focus monitor test mask," Society of Photo-Optical Instrumentation Engineers (SPIE) Conference Series, vol. 2197, 1994, pp. 541-549.

G. Robins et al., "Measuring optical image aberrations with pattern and probe based targets," Journal of Vacuum Science & Technology B, vol. 20, No. 1, 2002, pp. 338-343.

T. Terasawa et al., "Actinic phase defect detection and printability analysis for patterned EUVL mask," Proc. SPIE, vol. 7636, 2010, 763602, 10 pages.

T. Terasawa et al., "Development of actinic full-field EUV mask blank inspection tool at MIRAI-Selete," Proc. SPIE, vol. 7271, 2009, 727122, 8 pages.

(Continued)

*Primary Examiner* — Tarifur Chowdhury
*Assistant Examiner* — Isiaka Akanbi
(74) *Attorney, Agent, or Firm* — Keivan Razavi; Yuanmin Cai

(57) ABSTRACT

A method of fabricating an aberration monitor on a production mask used in photolithographic patterning of a semiconductor substrate is provided. The method may include placing a production mask within a nanomachine repair tool and generating, using the nanomachine repair tool, a phase shifting pattern within a region of the production mask.

20 Claims, 9 Drawing Sheets

(56) References Cited

OTHER PUBLICATIONS

E. E. Gallagher et al., "Extreme ultraviolet (EUV) multilayer defect compensation and EUV masks," U.S. Appl. No. 13/564,221, filed Aug. 1, 2012.

Pending U.S. Appl. No. 13/564,221, "Extreme Ultraviolet (EUV) Multilayer Defect Compensation and EUV Masks", date filed Aug. 1, 2012.

* cited by examiner

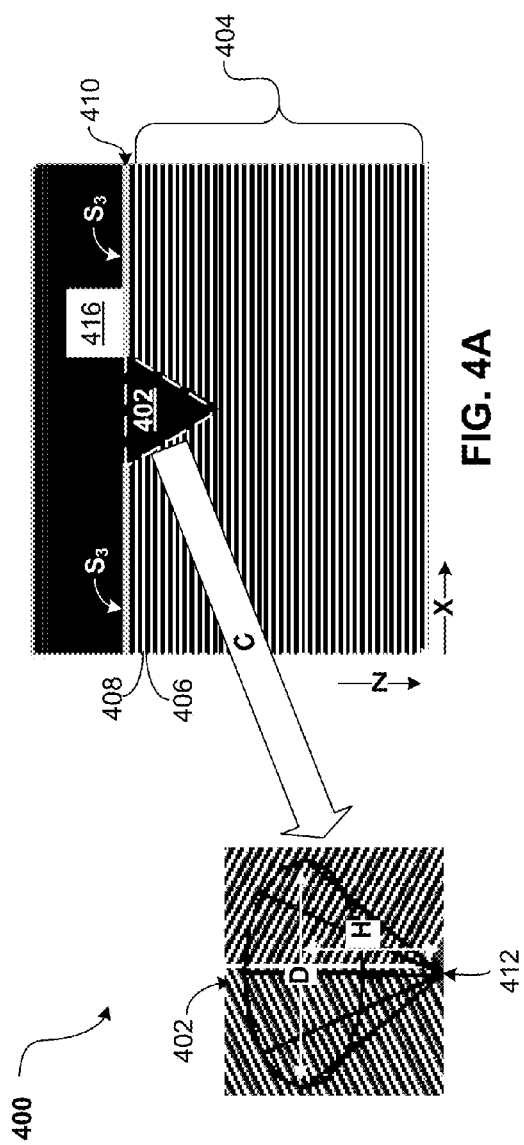
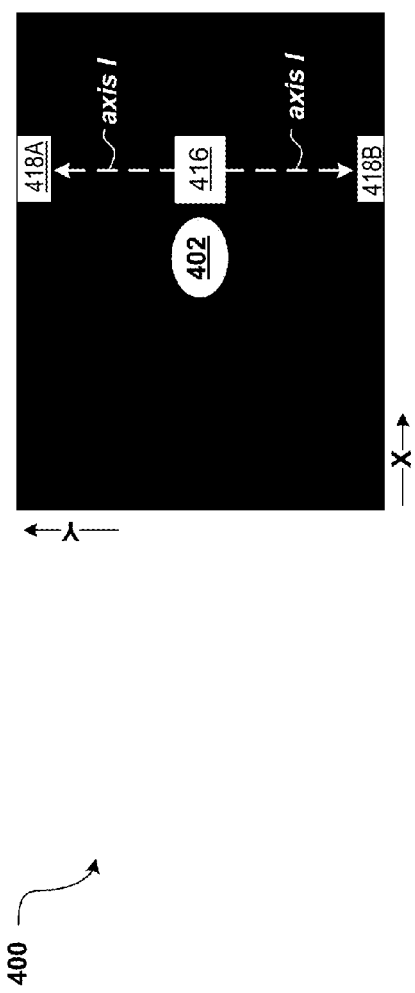
FIG. 4A
FIG. 4B

FABRICATION OF ON-PRODUCT ABERRATION MONITORS WITH NANOMACHINING

BACKGROUND a. Field of the Invention

The present invention generally relates to semiconductor manufacturing, and more particularly to focus/aberration monitors used in semiconductor manufacturing.

b. Background of Invention

A conventional deep ultraviolet (DUV) photomask is a transparent plate having a uniform thickness, whereby parts of the transparent plate are covered with non-transmitting (i.e., optically opaque) material in order to create a pattern on a semiconductor wafer when illuminated with, for example, ultra-violet (UV) light. The more recent introduction of extreme ultraviolet (EUV) lithography may require a completely reflective lithography system and thus the non-transmitting material of the photomask is placed on a multi-layer Bragg reflector. However, both DUV and EUV lithography tools that image the photomask patterns onto the semiconductor wafer have various optical components such as optical lenses and/or mirrors that are susceptible to aberrations. Aberrations are generally concerned with the lens state of the lithography tool. For example, focus variations (i.e., defocusing) associated with one or more lenses within the lithography tool may be one type of lens aberration that causes a distortion of the wavefront, which can in turn alter the feature size of a structure being imaged onto the semiconductor wafer surface using the patterned photomask. For instance, the heating of a lens as light passes through it may cause some warpage of the lens and, thus, some defocusing. Additionally, incorrect positioning of the wafer relative to the lens system can produce a defocus error.

Optimally, the semiconductor wafer surface is located at the focal plane of the lens that projects light onto the wafer's surface. However, due to aberration-based changes in the focal plane of the lens relative to the wafer surface, the resolution of the image generated on the wafer's surface varies. As previously discussed, this in turn may cause a change in the feature size and/or location placement of the patterned structures. Thus, aberration monitors may be utilized in order detect such aberrations caused by the lithography tool. Test masks be used in order to monitor aberrations and, therefore, ascertain the performance of the lithography tool.

However, test masks employing phase shifting patterns (e.g., 90° phase shifter) may be used solely for lithography tool evaluation and applied between the imaging photomasks. For example, a phase shifting pattern of a test mask may create a pattern (e.g., parallel lines) on the surface of the semiconductor wafer, whereby based on the geometry of the pattern (e.g., line spacing), a defocusing magnitude for the lithography tool may be determined.

Specifically, once a pattern is imaged by a photomask on the semiconductor wafer surface, the photomask may be removed and replaced by the test mask to evaluate the lithography tool. The test mask may then be removed and replaced by a subsequent patterned photomask used to image a circuit structure on the wafer. This process of using a separate test mask may delay the semiconductor manufacturing process and consequently, among other things, generate additional cost. Moreover, the test masks may be created by etching the phase shifting patterns into the glass substrate of the test mask, which may also contribute to the cost factor.

BRIEF SUMMARY

According to one or more embodiments, it may be advantageous, among other things, to provide enhanced aberration monitoring during photomask repair processes associated with production photomasks.

According to at least one exemplary embodiment, a method of fabricating an aberration monitor on a production mask used in photolithographic patterning of a semiconductor substrate is provided. The method may include placing a production mask within a nanomachine repair tool and generating, using the nanomachine repair tool, a phase shifting pattern within a region of the production mask. The method may further include generating the phase shifting pattern during the repairing of the production mask using the nanomachine repair tool.

According to at least one other exemplary embodiment, a method of evaluating a lithography tool using a production mask used in photolithographic patterning of a semiconductor substrate is provided. The method may include placing the production mask within the lithography tool, such that the production mask has a phase shifting pattern generated within a region of the production mask using a nanomachine repair tool. The phase shifting pattern is illuminated during the lithographic patterning, which generating an image pattern that is sensitive to aberrations. A geometric dimension of the generated image pattern is then measured and correlated to a de-focus value associated with the lithography tool.

According to yet another exemplary embodiment, a method of evaluating a lithography tool using a production mask used in photolithographic patterning of a semiconductor substrate is provided. The method may include placing the production mask in the lithography tool, whereby the production mask has a phase shifting material and patterned absorber lines. The patterned absorber lines are located on a top surface of the production mask and the phase shifting material is located between a pair of the absorber lines. The pair of the absorber lines and the phase shifting material are illuminated during the lithographic patterning such that an image pattern that is sensitive to aberrations is generated. A geometric dimension of the generated image pattern is then measured and correlated to a defocus value associated with the lithography tool.

BRIEF DESCRIPTION OF THE SEVERAL VIEWS OF THE DRAWINGS

FIG. 4A depicts a cross sectional view of a portion of a production mask having an aberration monitor, according to another embodiment;

FIG. 4B depicts a plan view of the production mask illustrated in FIG. 4A;

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

The following one or more exemplary embodiments describe the creation of aberration monitors on productions masks for evaluating, for example, focus variations (i.e., defocusing) associated with photolithography tools. Moreover, the aberration monitors may be created by atomic force microscope (AFM) nanomachine repair tools during a production mask repair process. The aberration monitors may be phase shifting patterns created on production masks, whereby the magnitude of the phase shifting caused by a phase shifting pattern on a production mask may depend on the volume of material that is nanomachined (e.g., see FIGS. 2A, 3A, and 4A-4B) or the volume of material deposited (e.g., see FIG. 5).

Figure 1:
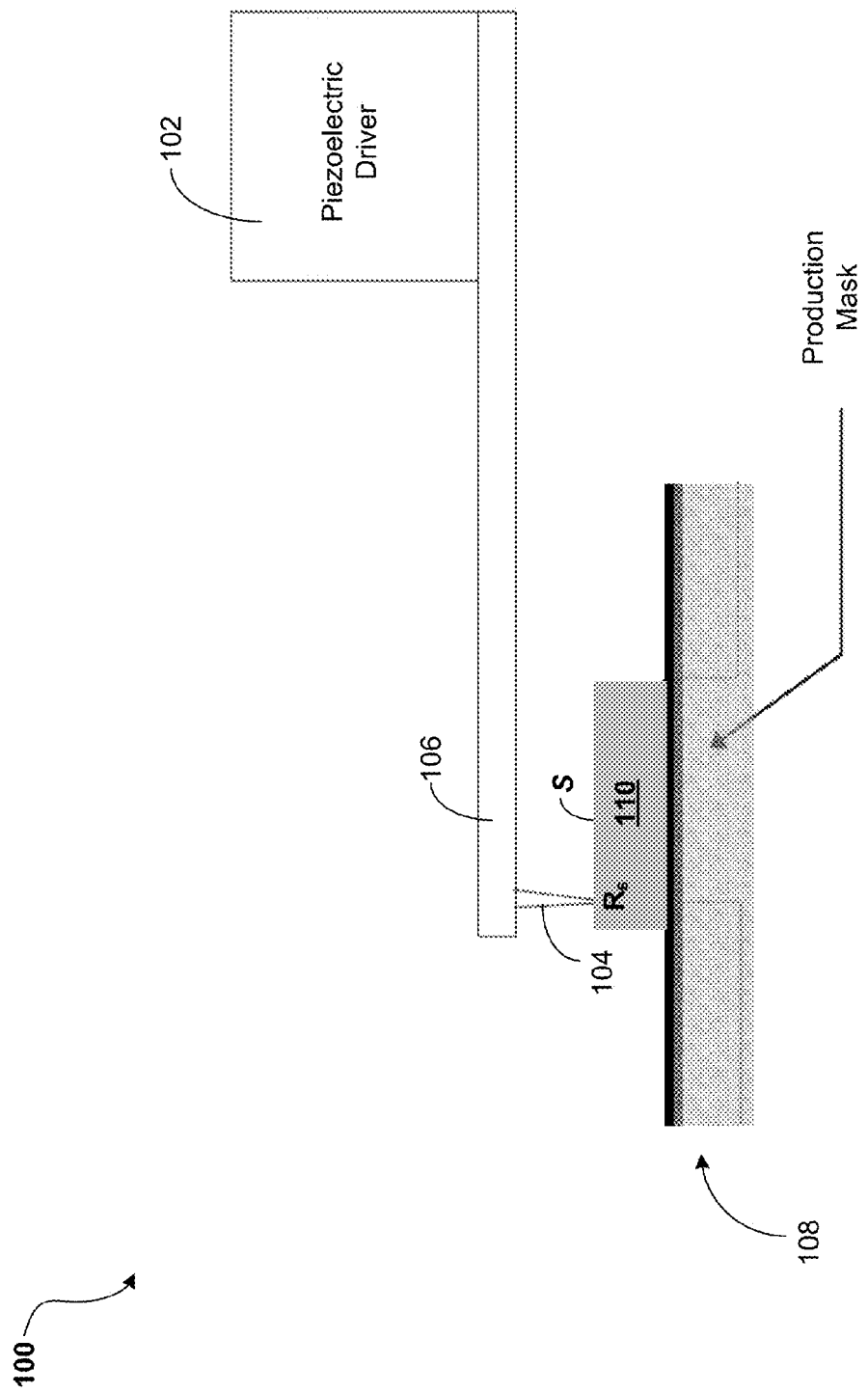
FIG. 1 is a block diagram illustrating a nanomachine repair tool, according to an embodiment.

FIG. 1 illustrates a block diagram 100 of, for example, an AFM nanomachining repair tool (e.g., Merlin® nanomachine by RAVE LLC) during a production mask repair, according to one embodiment. As depicted, within the nanomachining repair tool 100, a piezoelectric component 102 may be used to drive an AFM tip 104 via cantilever 106. The AFM tip 104 may be utilized to nanomachine select regions $R_s$ of a production mask 108. For example, a production mask repair may include a three-step process, whereby the AFM tip 104 is firstly used in a non-contact scan mode to determine the 3-dimensional (3D) topography of the production mask. During this scanning phase, the defect region is detected. Subsequently, the AFM tip 104 is used in a contact-mode to nanomachine the defective region. For example, region $R_s$ of production mask 108 may include a detected defect in the form of an uneven protruding surface on absorber material 110. The AFM tip 104 may then nanomachine the protrusion from the absorber 110 surface S using, for example, a cold mechanical process (e.g., NanoBit® by RAVE LLC). Finally, once the defect is nanomachined, any resulting debris may be removed using, for example, wet cleaning, $CO_2$ precision cleaning (e.g., Eco-Snow® by ECO-SNOW SYSTEMS), or contaminant pickup and removal technology (e.g., Bit-Clean® by RAVE LLC).

In addition to production mask repair, the above described exemplary nanomachine process may also be used to create aberration monitors on the production mask concurrently, prior to, or following the repair process. Also, the production mask serves to both photolithographically pattern device structures as well as provide the means for evaluating the photolithography tool used during the photolithographic process. The following embodiments described aberration monitors that may be formed on a production mask using a nanomachine repair tool such as the AFM nanomachine repair tool 100. The following described aberration monitor embodiments may be created during the repair process of the production mask. In the presence of a defect, the nanomachining could be used to compensate or repair, whereas aberration monitors would be created via the same nanomachining process in specific locations on the mask without the presence of a defect. If, however, a production mask repair is not necessary, the aberration monitor may solely be generated by the repair tool 100 to evaluate the lithography tool performance.

Figure 2A:
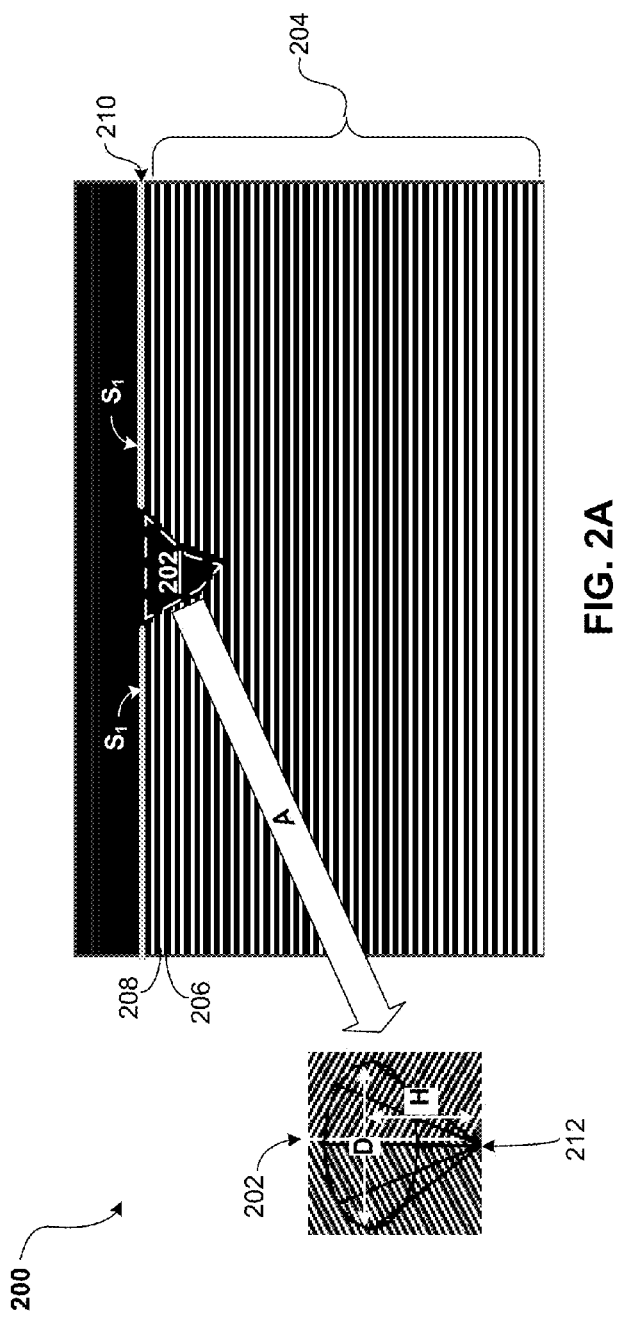
FIG. 2A depicts a cross sectional view of a portion of a production mask having an aberration monitor, according to one embodiment.

FIG. 2A depicts a cross sectional view of a portion of an EUV production mask 200 having an aberration monitor, according to one embodiment. The aberration monitor may be created by, for example, a nanomachining repair tool such as AFM nanomachining repair tool 100 (FIG. 1). Using AFM tip 104 (FIG. 1), a pit 202 (i.e., phase shifting pattern) may be generated within a region of the production mask 200. As described below, the formed pit acts as an aberration monitor which is sensitive to defocus. Thus, the AFM nanomachining repair tool 100 (FIG. 1) may generate the pit 202 in order to repair the production mask 200 or to act as an aberration monitor. In one implementation, the pit 202 may be generated using the AFM nanomachining repair tool 100 (FIG. 1) solely for creating an aberration monitor on the production mask 200. According to another implementation, the pit 202 may be generated using the AFM nanomachining repair tool 100 (FIG. 1) for creating an aberration monitor during the process of repairing the production mask 200.

The EUV production mask 200 typically includes a plurality of multilayer mirrors 204 having approximately forty (40) alternating bi-layers of Silicon (Si) 206 and Molybdenum (Mo) 208. Each Si layer 206 (i.e., denoted by darker layers) may have a thickness of about 4 nanometers (nm), while each of the Mo layers 208 (i.e., denoted by darker layers) has a thickness of about 2 nm. The top surface of the production mask 200 may be covered by a cap layer 210 of Ruthenium (Ru) material in order to protect the multilayer mirrors 204 from environmental contaminants.

The pit 202 extends between the top surface $S_1$ of the production mask 200 partially into the plurality of multilayer mirrors 204. The region where the pit 202 is formed may be located within a clear region of the production mask where no patterning is made. As indicated by arrow A, a perspective 3D expanded view illustrates the pit 202 having a substantially conical shape that includes a diameter (D) of about 70 nm at surface $S_1$, and a depth (H) of about 69 nm between surface $S_1$ and apex 212. In an alternative implementation (not shown), for example, the pit 202 may have a substantially conical shape that includes a square shape of about 70 nm at surface $S_1$, and a depth (H) of about 69 nm between surface $S_1$ and apex 212. The phase shifting magnitude of the created pit is generally determined by the volume of removed material.

In operation, during the lithography process, an optical source may generate, for example, an extreme ultra-violet (EUV) illumination signal (i.e., wavelength: 13.5 nm) for printing the production mask 200 pattern onto a layer of photoresist that is deposited on a substrate (e.g., semiconductor substrate). In addition to the imaged pattern, the pit 202 introduces a phase shift in the illumination signal that also generates an aberration sensitive image on the photoresist. For example, for an aberration such as focus variations (i.e., defocus), the physical dimensionality of the aberration sensitive image generated by the pit 202 changes with different defocus values. Therefore, based on a known change in the critical dimension of the aberration sensitive image, the amount of defocus for a lithography tool may be determined. This is described with the aid of FIG. 2B below.

Figure 2B:
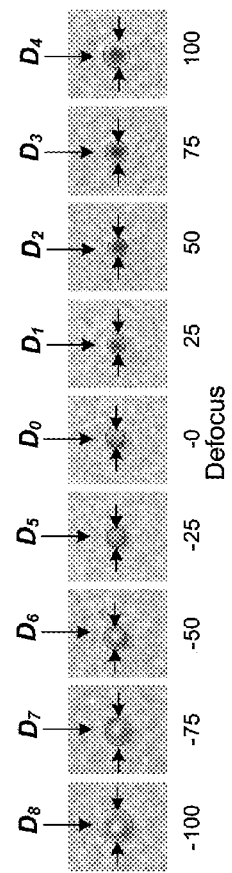
FIG. 2B illustrates a plan view of aberration sensitive images created by the aberration monitor of FIG. 2A during calibration.

FIG. 2B illustrates a plan view of exemplary aberration sensitive images created by the aberration monitor (i.e., pit 202) of FIG. 2A during calibration. As depicted, pillar shaped aberration sensitive images 215 are created, whereby a scanning electron microscope (SEM) may be utilized to measure the diameter of the images 215 as a function of the defocus values of the lithography tool used to generate the images on a photoresist. This is a calibration phase used for correlating the aberration sensitive images 215 with a particular defocus value. The calibration may be done when the lithography tool's defocusing settings are according to specification. For example, when the defocus is set to '0,' the actual tool's defocus is at, or within a specified tolerance of, the set defocus (i.e., '0'). Typically, the pattern may be exposed with multiple dose and defocus values to map out the full topography of the defocus-sensitive image in resist.

For example, at a defocus value of '0', the pillar may have a measured diameter of $D_0$. At defocus values of '25 nm, 50 nm, 75 nm, and 100 nm', the pillars may have measured diameters of $D_1$-$D_4$, respectively. Also, at defocus values of '-25 nm, -50 nm, -75 nm, and -100 nm', the pillars may have measured diameters of $D_5$-$D_8$, respectively.

During this calibration phase, each defocusing and corresponding diameter measurement using the SEM may be carried out on a photoresist layer of a separate die (e.g., a semiconductor die) on a wafer (e.g., a semiconductor wafer). For example, during the defocus value of '0' and the corresponding diameter of $D_0$, a layer of photoresist $P_1$ on die 1 may be photolithographically imaged by the lithography tool using the production mask 200 having the aberration monitor (i.e., pit 202). Once this measurement is complete, during the next defocus value of '25 nm' and the corresponding diameter of $D_1$, the layer of photoresist $P_1$ on die 2 may be photolithographically imaged by the lithography tool using the production mask 200 having the aberration monitor (i.e., pit 202). This process continues for all defocus and corresponding diameter measurements. Thus, if ten (10) measurements are taken, ten (10) different focus settings on the wafer may be exposed during calibration. Typically, a focus-exposure matrix may be exposed to obtain images from multiple doses as well as defocus settings.

Once this calibration is complete, the production mask 200 may utilize the pit 202 aberration monitor to continuously evaluate the lithography tool. For example, in operation, the optimum defocus value for the lithography tool may be determined to be '-25 nm'. Thus, prior to patterning a substrate, the lithography tool is set to its optimum defocus value of '-25 nm'. Once the substrate is patterned using the production mask 200, the pit 202 generates the aberration sensitive pillar. Using, for example, a SEM, the diameter $D'_5$ of the pillar corresponding to the defocus value of '-25 nm' is determined. During calibration, for a defocus value of '-25 nm', the diameter of the pillar was, however, determined to be $D_5$. If the newly measured diameter value of $D'_5$ is the same as, or within a predetermined range of (e.g., 5%) of, the calibrated pillar diameter of $D_5$, the lithography tool may be operating within the required tolerances and no further action may be taken. Alternatively, if the newly measured diameter value of $D'_5$ is outside the predetermined range of (e.g., 5%) of the calibrated column diameter of $D_5$, the lithography tool defocusing setting may be out of calibration and require attention in the form of, for example, a re-alignment of the optics (i.e., lenses etc.). Such errors in defocusing may be generated by, for example, thermal issues relating to the optics, improper wafer positioning, and/or misaligned optics caused by impact.

Figure 3A:
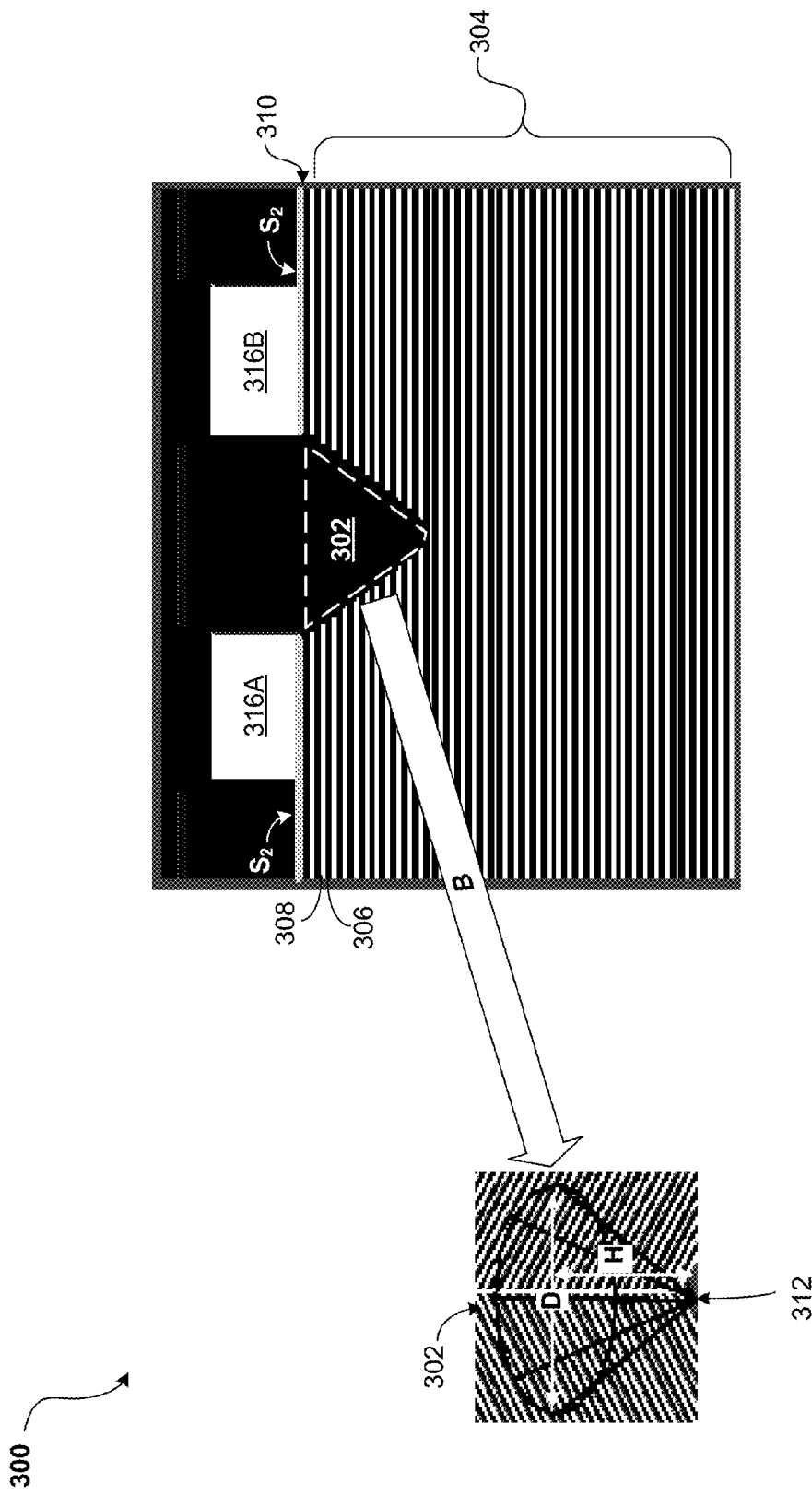
FIG. 3A depicts a cross sectional view of a portion of a production mask having an aberration monitor, according to another embodiment.

FIG. 3A depicts a cross sectional view of a portion of a production mask 300 having an aberration monitor, according to another embodiment. The aberration monitor may be created by, for example, a nanomachining repair tool such as AFM nanomachining repair tool 100 (FIG. 1). Using AFM tip 104 (FIG. 1), a pit 302 (i.e., phase shifting pattern) may be generated within a region (i.e., a repair location) of the production mask 300. As described below, the formed pit acts as an aberration monitor. Thus, the AFM nanomachining repair tool 100 (FIG. 1) may generate the pit 302 in order to repair the production mask 300 or to act as an aberration monitor. In one implementation, the pit 302 may be generated using the AFM nanomachining repair tool 100 (FIG. 1) solely for creating an aberration monitor on the production mask 300. According to another implementation, the pit 302 may be generated using the AFM nanomachining repair tool 100 (FIG. 1) for creating an aberration monitor during the process of repairing the production mask 300.

The production mask 300 may also include a plurality of multilayer mirrors 304 having approximately forty (40) alternating layers of Silicon (Si) 206 and Molybdenum (Mo) 208. Each Si layer 206 (i.e., denoted by darker layers) may have a thickness of about 4 nanometers (nm), while each of the Mo layers 208 (i.e., denoted by lighter layers) has a thickness of about 2 nm. The top surface of the production mask 300 may be covered by a cap layer 310 of Ruthenium (Ru) material in order to protect the multilayer mirrors 304 from environmental contaminants.

The pit 302 extends between the top surface $S_2$ of the production mask 300 partially into the plurality of multilayer mirrors 304. The region where the pit 302 is formed may be located between and adjacent to an absorber pair 316A, 316B corresponding to the production mask 300. The plurality of multilayer mirrors 304 and the absorber pair 316A, 316B of the production mask 300 generate a line and space pattern on a photoresist layer when illuminated. Each of the absorbers 316A, 316B may be formed from a layer of Tantalum Boron Nitride (TaBN), have a thickness of about 60-70 nm, and have a width that depends on the desired line and space pattern. As indicated by arrow B, a perspective 3D expanded view illustrates the pit 302 having a substantially conical shape that includes a diameter (D) of about 70 nm at surface $S_2$, and a depth (H) of about 100 nm between surface $S_2$ and apex 312.

In operation, during the lithography process, an optical source may generate, for example, an extreme ultra-violet (EUV) illumination signal (i.e., wavelength: 13.5 nm) for printing the production mask 300 line and space pattern onto a layer of photoresist that is deposited on a substrate (e.g., semiconductor substrate). In addition to the imaged line and space pattern, the pit 302 introduces a phase shift in the illumination signal that also generates an aberration sensitive image within the space region of the line and space image printed on the photoresist. For example, for an aberration such as focus variations (i.e., defocus), the physical dimensionality of the aberration sensitive image generated by the pit 302 changes with different defocus values. Therefore, as previously indicated, based on a known change in the critical dimension of the aberration sensitive image, the amount of defocus for a lithography tool may be determined. This is described with the aid of FIG. 3B below.

Figure 3B:
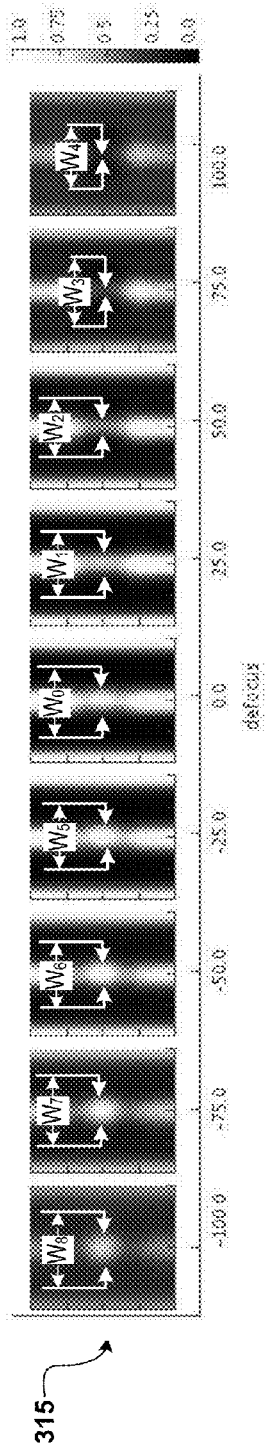
FIG. 3B illustrates a plan view of aberration sensitive images created by the aberration monitor of FIG. 3A during calibration.

FIG. 3B illustrates a plan view of exemplary aberration sensitive images created by the aberration monitor (i.e., pit 302) of FIG. 3A during calibration. As depicted, elongate line shaped aberration sensitive images 315 are created, whereby a scanning electron microscope (SEM) may be utilized to measure the line width (W) of the images 315 as a function of the defocus values of the lithography tool used to generate the images on a photoresist. The elongate line shaped aberration sensitive images 315 include a bright spot shape at the center portion, whereby the line width (W) of the images 315 are measured at this spot. This is a calibration phase used for correlating the aberration sensitive images 315 with a particular defocus value. The calibration may be done when the lithography tool's defocusing settings are according to specification. For example, at a defocus value of '0', the elongate line may have a width of $W_0$. At defocus values of '25 nm, 50 nm, 75 nm, and 100 nm', the elongate line shaped images may have widths of $W_1$-$W_4$, respectively. Also, at defocus values of '−25 nm, −50 nm, −75 nm, and −100 nm', the elongate line shaped images may have widths of $W_5$-$W_8$, respectively.

During this calibration phase, each defocusing and corresponding width measurement using the SEM may be carried out on a photoresist layer of a separate die (e.g., a semiconductor die) on a wafer (e.g., a semiconductor wafer). For example, during the defocus value of '0' and the corresponding width of $W_0$, a layer of photoresist $P_1$ on die 1 may be photolithographically imaged by the lithography tool using the production mask 300 having the aberration monitor (i.e., pit 302). Once this measurement is complete, during the next defocus value of '25 nm' and the corresponding width of $W_1$, the layer of photoresist $P_1$ on die 2 may be photolithographically imaged by the lithography tool using the production mask 300 having the aberration monitor (i.e., pit 302). This process continues for all defocus and corresponding diameter measurements. Thus, if ten (10) measurements are taken, ten (10) dies on the wafer may be exposed during calibration.

Once this calibration is complete, the production mask 300 may utilize the pit 302 aberration monitor to continuously evaluate the lithography tool. For example, in operation, the optimum defocus value for the lithography tool may be determined to be '−25 nm'. Thus, prior to patterning a substrate, the lithography tool is set to its optimum defocus value of '−25 nm'. Once the substrate is patterned using the production mask 300, the pit 302 generates the aberration sensitive elongate line shape image. Using, for example, a SEM, the width $W'_5$ of the elongate line shaped image corresponding to the defocus value of '−25 nm' is determined. During calibration, for a defocus value of '−25 nm', the width of the elongate line shaped image was, however, determined to be $W_5$. If the newly measured width value of $W'_5$ is the same as, or within a predetermined range of (e.g., 5%) of, the calibrated line width of $W_5$, the lithography tool may be operating within the required tolerances and no further action may be taken. Alternatively, if the newly measured width value of $W'_5$ is outside the predetermined range of (e.g., 5%) the calibrated line width of $W_5$, the lithography tool may require attention in the form of, for example, a re-alignment of the optics (i.e., lenses etc.). Such errors in defocusing may be generated by, for example, thermal issues relating to the optics, vibrations, and/or misaligned optics caused by impact.

Figure 3C:
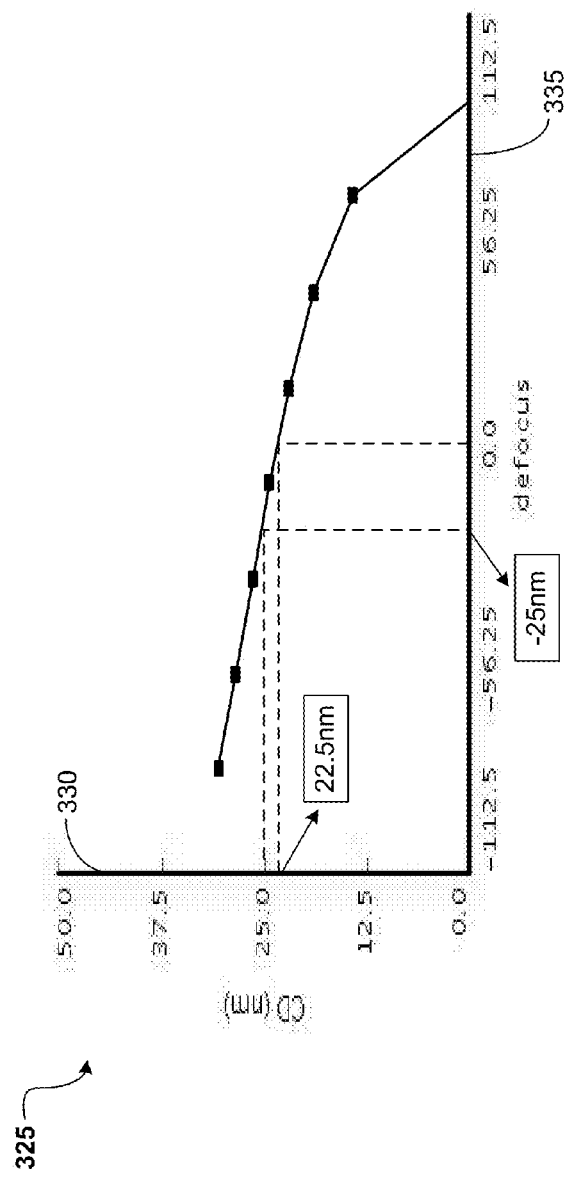
FIG. 3C illustrates a graphical representation of the calibration process depicted by FIG. 3B.

FIG. 3C illustrates a graphical representation of the exemplary aberration sensitive images created by the aberration monitor (i.e., pit 302) of FIG. 3A during calibration. Specifically, the defocus settings and corresponding width measurements of the elongate line shape images during calibration may be illustrated in graph 325. The Y-axis 330 of the graph 325 represents the line width values (i.e., CD) of the elongate line shape images (e.g., FIG. 3B: 315). The X-axis 335 of the graph 325 represents the defocus setting used during calibration.

For example, using graph 325, it may be determined that for an optimum defocus value of '0 nm', a width value (CD) of 22.5 nm corresponds to the elongate line shaped image created for a calibrated lithography tool. In operation, the production mask 300 may, however, create an elongate line shaped image having a measured width value of 25 nm using pit 302 (FIG. 3A). As depicted on graph 325, for a measured width value (CD) of 25 nm, a defocus value of '−25 nm' applies. The foregoing result may indicate that the lithography tool has a new defocus value of '−25 nm', which is indicative that the lithography tool is out of calibration by 25 nm based on the initial optimum defocus setting of '0 nm'.

FIG. 4A depicts a cross sectional view of a portion of a production mask 400 having an aberration monitor, according to another embodiment. FIG. 4B depicts a plan view of production mask 400. Referring to FIGS. 4A and 4B, the aberration monitor may be created by, for example, a nanomachining repair tool such as AFM nanomachining repair tool 100 (FIG. 1). Using AFM tip 104 (FIG. 1), a pit 402 (i.e., phase shifting pattern) may be generated within a region (i.e., a repair location) of the production mask 300. As described below, the formed pit in combination with the nearby absorber pillar 416 acts as an aberration monitor.

The production mask 400 may also include a plurality of multilayer mirrors 404 having approximately forty (40) alternating layers of Silicon (Si) 406 and Molybdenum (Mo) 408. Each Si layer 406 (i.e., denoted by darker layers) may have a thickness of about 4 nanometers (nm), while each of the Mo layers 208 (i.e., denoted by lighter layers) has a thickness of about 2 nm. The top surface of the production mask 400 may be covered by a cap layer 410 of Ruthenium (Ru) material in order to protect the multilayer mirrors 404 from environmental contaminants.

The pit 402 extends between the top surface $S_3$ of the production mask 400 partially into the plurality of multilayer mirrors 404. The region where the pit 402 is formed may be located adjacent to an absorber 416 corresponding to the production mask 400. Absorber 416 is located between absorber pair 418A and 418B, whereby the absorbers 416, 418A, 418B are located along the same line, as indicated by axis I. Each of the absorbers 316, 318A, 318B may be formed from a layer of Tantalum Boron Nitride (TaBN). As indicated by arrow C, a perspective 3D expanded view illustrates the pit 402 having a substantially conical shape that includes a diameter (D) of about 70 nm at surface $S_3$, and a depth (H) of about 100 nm between surface $S_3$ and apex 412.

In operation, during the lithography process, an optical source may generate, for example, an extreme ultra-violet (EUV) illumination signal (i.e., wavelength: 13.5 nm) for printing the production mask 400 pattern onto a layer of photoresist that is deposited on a substrate (e.g., semiconductor substrate). In addition to the imaged pattern, the pit 402 introduces a phase shift in the illumination signal that also generates an aberration sensitive image on the photoresist. For example, for an aberration such as focus variations (i.e., defocus), the physical dimensionality and placement of the aberration sensitive image generated by the pit 402 changes with different defocus values. Therefore, based on a known change in the placement of the aberration sensitive image, the amount of defocus for a lithography tool may be determined. This is described with the aid of FIG. 4C below.

Figure 4C:
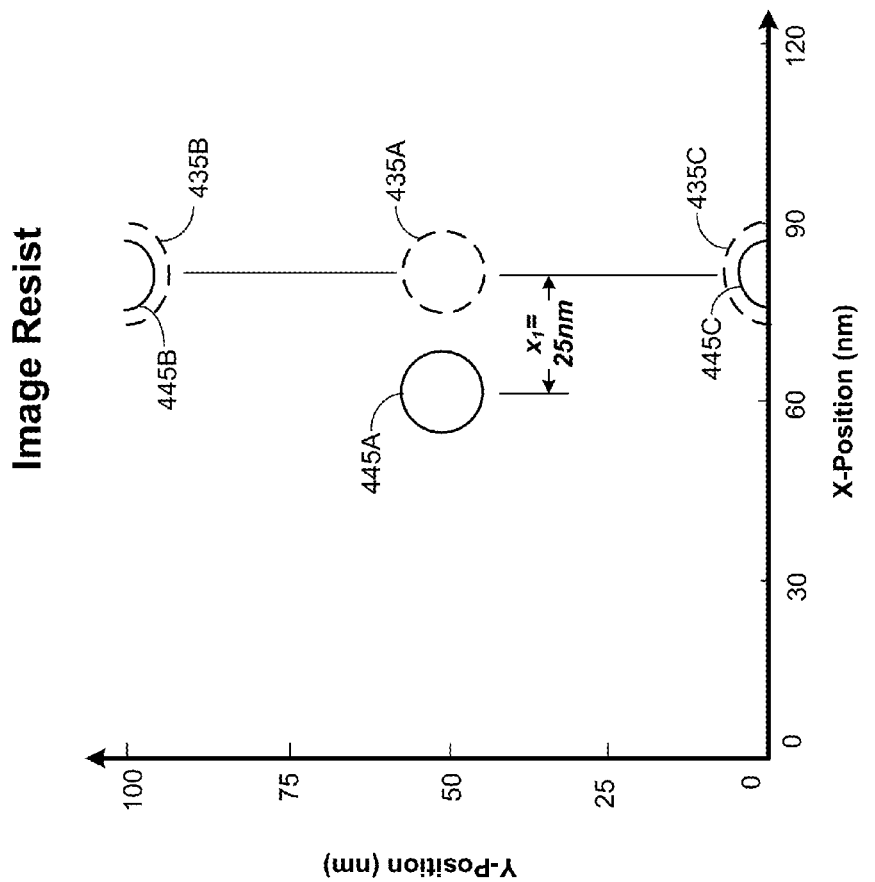
FIG. 4C illustrates a plan view of aberration sensitive images created by the aberration monitor of FIG. 4A during calibration.

FIG. 4C illustrates a plan view of exemplary aberration sensitive images created by the aberration monitor (i.e., pit 402) of FIG. 4A during calibration. As depicted, multiple circular shaped aberration sensitive images 415 are created based on the absorbers 316, 318A, 318B and the pit 402. A scanning electron microscope (SEM) may be utilized to measure the position of the circular images 415 as a function of the defocus values of the lithography tool used to generate the images on a photoresist. This is a calibration phase used for correlating the aberration sensitive images 415 with a particular defocus value. The calibration may be done when the lithography tool's defocusing settings are according to specification. For example, when the defocus is set to '0 nm,' the actual tool's defocus is at, or within a specified tolerance of, the set defocus (i.e., '0 nm').

For illustrative brevity, two exemplary generated circular shaped images are depicted. For example, circular shaped aberration sensitive images 435A-435C are generated based on a defocus value of '0 nm'. Thus, center circular image 435A is aligned with respect to reference circular images 435B and 435C. Circular images 435B and 435C are denoted as reference images because they remain substantial fixed and are generated by aligned absorbers 318A and 318B. The position of center circular image 435A relative to reference circular images 435B and 435C may depend on the defocus value. The center circular image 435A may be generated by the pit 402 and adjacent absorber 435A. In this example, for a defocus of '0 nm', the center circular image 435A is substantially aligned relative to reference circular images 435B and 435C, and, thus, there is no offset (i.e., x=0). Alternatively, according to another example, circular shaped aberration sensitive images 445A-445C may be generated based on a defocus value of '25 nm'. Here, the center circular image 435A is offset (i.e., $x=x_1=25$ nm) relative to reference circular images 445B and 445C. Thus, during the calibration process, the offset values of the center circular image relative to the reference circular images are recorded for various defocus values.

Once this calibration is complete, the production mask 400 may utilize the pit 402 aberration monitor to continuously evaluate the lithography tool. For example, in operation, the optimum defocus value for the lithography tool may be determined to be '0 nm.' Thus, prior to patterning a substrate, the lithography tool is set to its optimum defocus value of '0 nm.' Once the substrate is patterned using the production mask 400, the pit 402 also generates the aberration sensitive circular images. Using, for example, a SEM, the offset $x_1'$ of the center circular image relative to the reference circular images corresponding to the defocus value of '0 nm' is determined. During calibration, for a defocus value of '0 nm', the offset was, however, determined to be zero (i.e., $x_1=0$). If the newly measured offset value of $x_1'$ is the same as, or within a predetermined range of (e.g., 5%) the calibrated offset of zero, the lithography tool may be operating within the required tolerances and no further action may be taken. Alternatively, if the newly measured offset value of $x_1'$ is outside the predetermined range of (e.g., 5%) of the calibrated offset of zero, the lithography tool may require attention in the form of, for example, a re-alignment of the optics (i.e., lenses etc.). Such errors in defocusing may be generated by, for example, thermal issues relating to the optics, vibrations, and/or misaligned optics caused by impact. For example, if the offset measurement (i.e., x) of the center circular image relative to the reference circular images is 25 nm, then, based on the calibration measurements, it may be apparent that the lithography tool is out of focus by 25 nm. This is because, at a calibrated offset value of 25 nm (i.e., $x_1=25$ nm), the defocus was determined to be '25 nm'.

Figure 4D:
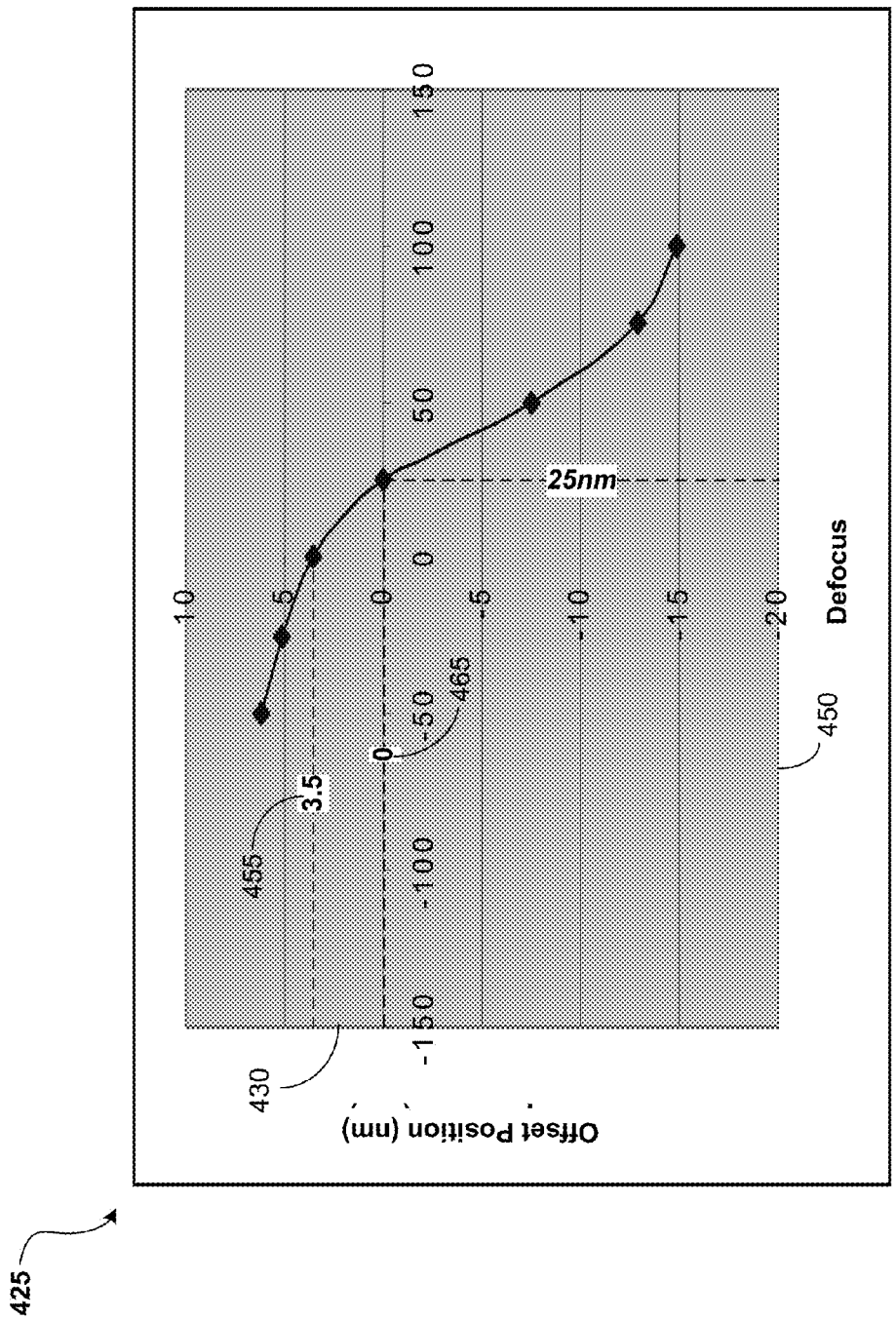
FIG. 4D illustrates a graphical representation of the calibration process depicted by FIG. 4C.

FIG. 4D illustrates a graphical representation of the exemplary aberration sensitive images created by the aberration monitor (i.e., pit 402) of FIG. 4A during calibration. Specifically, the defocus settings and corresponding offset measurements of the multiple circular shaped images during calibration may be illustrated in graph 425. The Y-axis 430 of the graph 425 represents the offset values (i.e., x) of the center circular shaped images (e.g., FIG. 4C: 445A) relative to the reference circular images (e.g., FIG. 4C: 445B-445C). The X-axis 450 of the graph 425 represents the defocus settings used during calibration.

For example, using graph 425, it may be determined that for an optimum defocus value of '0 nm', an offset value of 3.5 nm, as indicated at 455, may be expected for a calibrated lithography tool. In operation, the production mask 400 may, however, create circular images having an offset value of 0 nm using pit 402 (FIG. 4A). As depicted on graph 425, for a measured offset value of 0 nm, as indicated at 465, a defocus value of '25 nm' applies. The foregoing result may indicate that the lithography tool has a new defocus value of '25 nm', which is indicative that the lithography tool is out of calibration by 25 nm based on the initial optimum defocus setting of '0 nm'.

Figure 5:
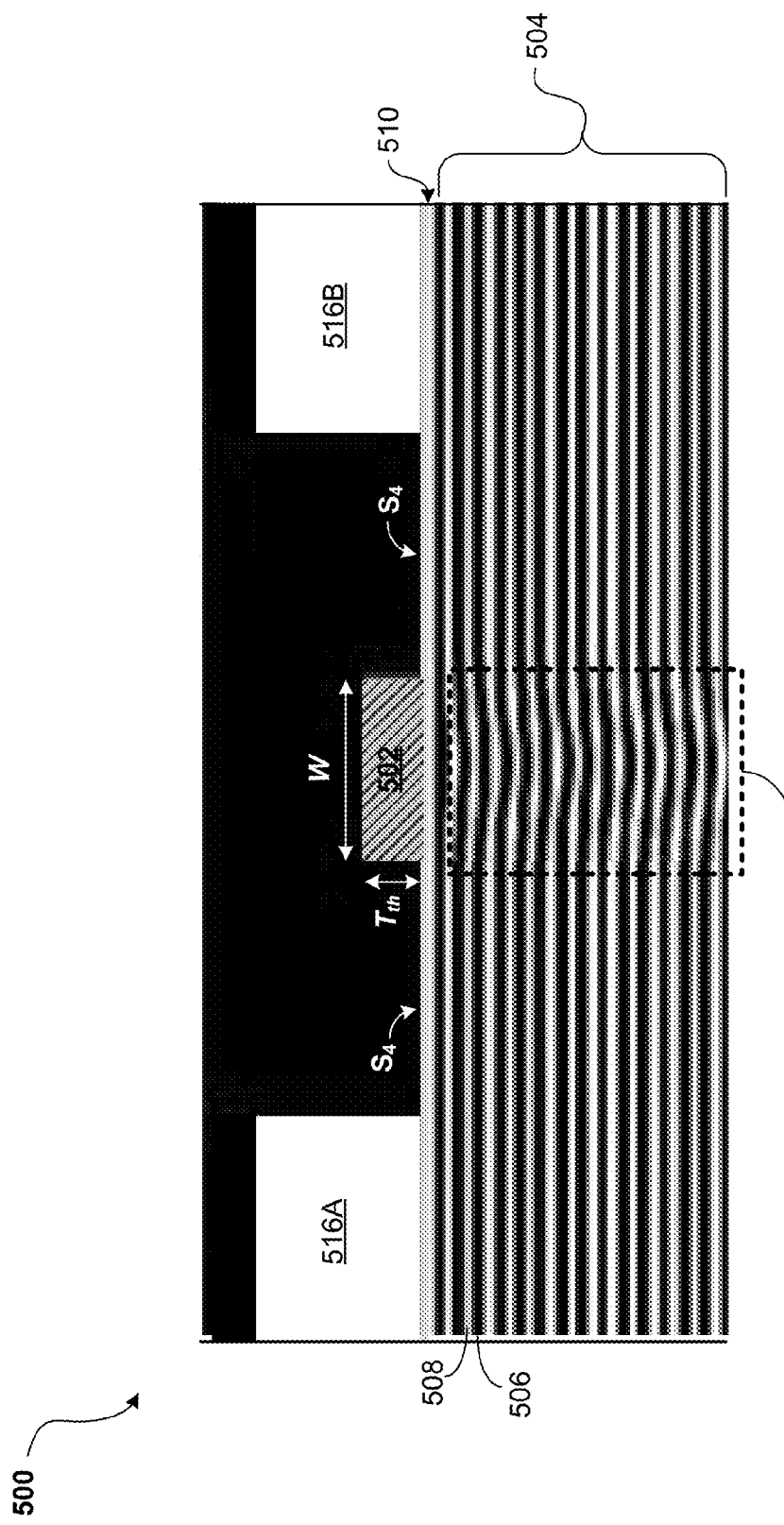
FIG. 5 depicts a cross sectional view of a portion of a production mask having an aberration monitor, according to yet another embodiment.

FIG. 5 depicts a cross sectional view of a portion of a production mask 500 having an aberration monitor, according to yet another embodiment. The aberration monitor may be created by, for example, the targeted deposition of a phase shifting layer of material 502 (i.e., phase shifting pattern) within a region (i.e., a repair location) of the production mask 500. As described below, the deposited layer acts as an aberration monitor by creating a phase shift in the incident optical illumination signal generated by the lithography tool. Alternatively, the deposited layer 502 may also facilitate the repair of an existing defect, as indicated by region 501, in the production mask 500 by generating a phase shift that compensates for a phase shift caused by the defect.

The production mask 500 may also include a plurality of multilayer mirrors 504 having approximately forty (40) alternating layers of Silicon (Si) 506 and Molybdenum (Mo) 508. Each Si layer 506 (i.e., denoted by darker layers) may have a thickness of about 4 nanometers (nm), while each of the Mo layers 508 (i.e., denoted by lighter layers) has a thickness of about 2 nm. The top surface of the production mask 500 may be covered by a cap layer 510 of Ruthenium (Ru) material in order to protect the multilayer mirrors 504 from environmental contaminants.

The phase shifting layer 502 is deposited on the top surface $S_4$ of the production mask 500, and located between and adjacent to an absorber pair 516A, 516B corresponding to the production mask 500. The plurality of multilayer mirrors 504 and the absorber pair 516A, 516B of the production mask 500 generate a line and space pattern on a photoresist layer when illuminated. Each of the absorbers 516A, 516B may be formed from a layer of Tantalum Boron Nitride (TaBN), have a thickness of about 60-70 nm, and have a width that depends on the desired line and space pattern. The phase shifting layer 502 may include a layer Ruthenium (Ru) having a thickness $T_{th}$ of approximately 40 nm and a width W of about 50-60 nm. Although, Ruthenium may be selected for its high transmission of light and ability to generate phase shifting, other comparable material may be used within the production mask 500.

As with the other embodiments (FIGS. 2-4), the embodiment of FIG. 5 also generates aberration sensitive images as a function of different defocus settings on a lithography tool. Thus, the same calibration and methods of use apply.

Figure 6:
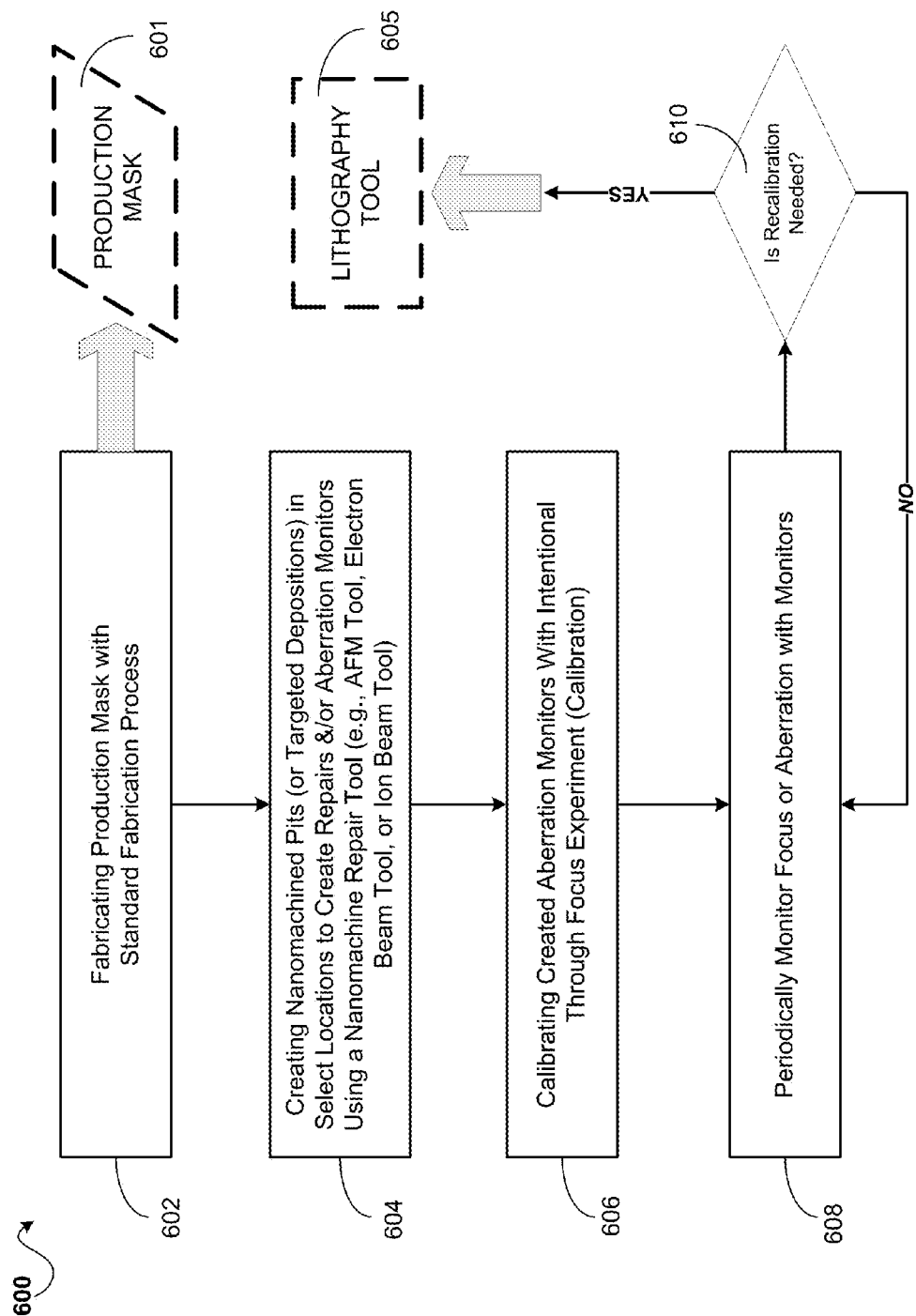
FIG. 6 is a flow diagram corresponding to a process of creating the exemplary aberration monitor embodiments.

FIG. 6 is a flow diagram 600 corresponding to a process of creating the exemplary aberration monitor embodiments. At 602, a lithography production mask such as 601 may be fabricated using conventional processes. At 604, a nanomachine repair tool such as 100 (FIG. 1) may be used to repair a defect in the fabricated production mask 601. The defect repair may also take the form (i.e., pit structures) of the embodiments of FIGS. 2A, 3A, and 4A. In addition to repairing defects in the production mask, the embodiments of FIGS. 2A, 3A, and 4A may also be generated using the nanomachine repair tool 100 to provide aberration monitoring through the generation of images (i.e., during lithographic process) on a photoresist layer that are indicative of lens aberrations such as focus variations (i.e., defocus errors). Alternatively, the embodiments of FIGS. 2A, 3A, and 4A may be generated by the nanomachine repair tool 100 solely for providing aberration monitoring, without the need to utilize the nanomachine repair tool 100 for the purpose of repairing the production mask 601.

Defect repair may additionally take the form (i.e., target deposited structures) of the deposited embodiment of FIG. 5. Thus, in addition to repairing the production mask, the embodiment of FIG. 5 may also facilitate providing aberration monitoring through the generation of images (i.e., during lithographic process) on a photoresist layer that are indicative of lens aberrations such as focus variations (i.e., defocus errors).

At 606, the aberration monitors in the form of either a nanomachined pit or deposited layer (e.g., layer of Ru) may be used to calibrate the lithograph tool 605, whereby, as described above, one or more physical dimensions of the image generated by the aberration monitor on photoresist are measured as a function of defocus value settings applied to the lithography tool 605.

At 608, following the calibration of the lithography tool 605 with a formed aberration monitor (606), the lithography tool is monitored during subsequent device manufacturing when, for example, a device structure pattern is lithographically printed on device substrates (e.g., semiconductor substrate) using the production mask 601. As previously described, each time the production mask 601 is used (following calibration), the aberration sensitive images generated by the aberration monitor (e.g., FIG. 2A, 3A, 4A, or 5) are measured and compared against the calibrated measurements (606) in order to determine whether the lithography tool 605 is operating within specification.

Based on this monitoring (608), at 610 it may be evaluated whether, for example, the lithography tool 605 needs a recalibration (i.e., servicing) of its optical arrangement. The monitoring 608 and evaluation 610 continues until, for example, it is determined that the lithography tool 605 defocus value is shifted beyond its optimum set value by a predetermined amount or percentage. In addition to using an AFM nanomachine repair tool (e.g., FIG. 1), other nanomachine repair tools such as an electron beam repair tool or an ion beam repair tool may be utilized for nanomachining the production masks.

The method of producing the aberration monitors described above may also be applicable in producing various other aberration monitors. Whereas the formation of phase shifting patterns in previous attempts have typically been done with conventional etch processes, these foregoing topographies could be created with the nanomachining process described above.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the one or more embodiment, the practical application or technical improvement over technologies found in the marketplace, or to enable others of ordinary skill in the art to understand the embodiments disclosed herein.

What is claimed is:

1. A method of fabricating an aberration monitor on a production mask used in photolithographic patterning of a semiconductor substrate, the method comprising:

placing a production mask within a nanomachine repair tool; and generating, using the nanomachine repair tool, a phase shifting pattern within a region of the production mask, the phase shifting pattern both repairing the production mask and providing an aberration monitor that generates an aberration sensitive image during the photolithographic patterning of the semiconductor substrate using a photolithographic tool, wherein the generated aberration sensitive image includes a measured diameter that is compared with calibrated measurements associated with the lithographic tool for determining a recalibration of the lithographic tool.

2. The method of claim 1, wherein the generating, using a nanomachine repair tool, of the phase shifting pattern occurs during a repair of the production mask using the nanomachine repair tool.

3. The method of claim 1, wherein the nanomachine repair tool comprises an atomic force microscope (AFM) repair tool.

4. The method of claim 1, wherein the nanomachine repair tool comprises one of an electron beam repair tool and an ion beam repair tool.

5. The method of claim 1,
wherein the generating of the phase shifting pattern comprises machining, using the nanomachine repair tool, a pit that extends from a top surface of the production mask partially into a plurality of multilayer mirrors corresponding to the production mask, the region where the pit is located being within a clear region of the production mask, and
wherein the pit projects a pillar shaped image on the semiconductor substrate, the pillar shaped image having dimensions that vary with defocus variations of a lithography tool used to image the production mask on the semiconductor substrate.

6. The method of claim 5, wherein the pit comprises a substantially conical shape having a diameter of about 70 nanometers and having a depth of about 70 nanometers.

7. The method of claim 5, wherein the plurality of multilayer mirrors comprises alternating layers of Silicon (Si) and Molybdenum (Mo).

8. The method of claim 1,
wherein the generating of the phase shifting pattern comprises machining, using the nanomachine repair tool, a pit that extends from a top surface of the production mask partially into a plurality of multilayer mirrors corresponding to the production mask, the pit located between an absorber pair, and
wherein the pit projects the aberration sensitive image as an elongate line shaped image during the photolithographic patterning of the semiconductor substrate using the photolithographic tool, wherein the projected elongate line shaped image includes a measured width that is compared with calibrated measurements associated with the lithographic tool for determining the recalibration of the lithographic tool.

9. The method of claim 8, wherein the pit comprises a substantially conical shape having an apex and an opening diameter, the opening diameter located at the top surface of the production mask and the apex located partially within the plurality of multilayer mirrors.

10. The method of claim 9, wherein the opening diameter is about 70 nanometers and the apex is at a depth of about 100 nanometers from the top surface.

11. The method of claim 1,
wherein the generating of the phase shifting pattern comprises machining, using the nanomachine repair tool, a pit that extends from a top surface of the production mask partially into a plurality of multilayer mirrors corresponding to the production mask, the pit located adjacent to an absorber, the absorber located between a reference absorber pair, and
wherein the pit projects the aberration sensitive image as a circular shaped image during the photolithographic patterning of the semiconductor substrate using the photolithographic tool, wherein the projected circular shaped image includes a measured lateral displacement that is compared with calibrated measurements associated with the lithographic tool for determining the recalibration of the lithographic tool.

12. The method of claim 11, wherein the pit comprises a substantially conical shape having an apex and an opening diameter, the opening diameter located at the top surface of the production mask and the apex located partially within the plurality of multilayer mirrors.

13. A method of evaluating a lithography tool using a production mask used in photolithographic patterning of a semiconductor substrate, the method comprising:
placing the production mask within the lithography tool, the production mask having a phase shifting pattern generated within a region of the production mask using a nanomachine repair tool;
illuminating the phase shifting pattern during the lithographic patterning and generating an image pattern that is sensitive to lens aberrations corresponding to the lithography tool;
measuring a geometric dimension of the generated image pattern; and
correlating the measured geometric dimension with calibrated measurements associated with the lithography tool for determining a recalibration of the lithography tool, the phase shifting pattern both repairing the production mask and determining the recalibration of the lithography tool during the photolithographic patterning of a semiconductor substrate,
wherein the correlating of the measured geometric dimension with the calibrated measurements associated with the lithography tool determines the recalibration of the lithography tool.

14. The method of claim 13, wherein the phase shifting pattern is generated during a repair of the production mask using the nanomachine repair tool.

15. The method of claim 13,
wherein the generating of the phase shifting pattern comprises machining, using the nanomachine repair tool, a pit that extends from the surface of the production mask partially into a plurality of multilayer mirrors corresponding to the production mask, the region where the pit is located being within a clear region of the production mask; and
wherein the image pattern includes a pillar shaped image on the semiconductor substrate, the pillar shaped image having a diameter that varies with defocus of a lithography tool used to image the production mask on the semiconductor substrate.

16. The method of claim 13,
wherein the generating of the phase shifting pattern comprises machining, using the nanomachine repair tool, a pit that extends from a top surface of the production mask partially into a plurality of multilayer mirrors corresponding to the production mask, the pit located between an absorber pair that generates a line and space pattern image in conjunction with the plurality of multilayer mirrors; and
wherein the image pattern includes an elongate line shaped image within the generated line and space pattern image on the semiconductor substrate, the elongate line shaped image having a line width that varies with defocus variations of a lithography tool used to image the production mask on the semiconductor substrate.

17. The method of claim 13,
wherein the generating of the phase shifting pattern comprises machining, using the nanomachine repair tool, a pit that extends from a top surface of the production mask partially into a plurality of multilayer mirrors corresponding to the production mask, the pit located adjacent to an absorber, the absorber located between a reference absorber pair; and
wherein the image pattern includes a circular shaped image that is laterally displaced with respect to a pair of circular images corresponding to the reference absorber pair based on defocus variations of a lithography tool used to image the production mask on the semiconductor substrate.

18. A method of evaluating a lithography tool using a production mask used in photolithographic patterning of a semiconductor substrate, the method comprising:
placing the production mask in the lithography tool, the production mask having a phase shifting material and patterned absorber lines, the patterned absorber lines located on a top surface of the production mask and the phase shifting material located between a pair of the absorber lines;
illuminating the pair of the absorber lines and the phase shifting material during the lithographic patterning and generating an image pattern that is sensitive to lens aberrations corresponding to the lithography tool;
measuring a geometric dimension of the generated image pattern; and
correlating the measured geometric dimension with calibrated measurements associated with the lithography tool for determining a recalibration of the lithography tool, the phase shifting material both repairing the production mask and determining the recalibration of the lithography tool during the photolithographic patterning of a semiconductor substrate,
wherein the correlating of the measured geometric dimension with the calibrated measurements associated with the lithography tool determines the recalibration of the lithography tool.

19. The method of claim 18, wherein the phase shifting material is Ruthenium (Ru).

20. The method of claim 18, wherein the phase shifting material comprises a material that exhibits a reduced loss in optical signal transmission and an increased shift in phase.

* * * * *